(12) United States Patent
Pinkerton et al.

(10) Patent No.: US 9,440,881 B2
(45) Date of Patent: Sep. 13, 2016

(54) MICRO-REBAR CONCRETE REINFORCEMENT SYSTEM

(71) Applicants: Luke Pinkerton, Ann Arbor, MI (US); Joseph L. Stecher, Minneapolis, MN (US); Jeffrey Novak, Kennesaw, GA (US)

(72) Inventors: Luke Pinkerton, Ann Arbor, MI (US); Joseph L. Stecher, Minneapolis, MN (US); Jeffrey Novak, Kennesaw, GA (US)

(73) Assignee: Polytorx, LLC, Ann Arbor, MI (US)

( * ) Notice: Subject to any disclaimer, the term of this patent is extended or adjusted under 35 U.S.C. 154(b) by 0 days.

(21) Appl. No.: 14/652,541

(22) PCT Filed: Dec. 18, 2013

(86) PCT No.: PCT/US2013/076061
§ 371 (c)(1),
(2) Date: Jun. 16, 2015

(87) PCT Pub. No.: WO2014/100142
PCT Pub. Date: Jun. 24, 2014

(65) Prior Publication Data
US 2015/0329424 A1 Nov. 19, 2015

Related U.S. Application Data

(60) Provisional application No. 61/738,483, filed on Dec. 18, 2012.

(51) Int. Cl.
| | | |
|---|---|---|
| G01B 5/30 | (2006.01) |
| C04B 14/48 | (2006.01) |
| G01N 33/38 | (2006.01) |
| G01B 7/24 | (2006.01) |
| C04B 28/02 | (2006.01) |
| C04B 20/00 | (2006.01) |
| E04C 5/01 | (2006.01) |

(52) U.S. Cl.
CPC ........... *C04B 14/48* (2013.01); *C04B 20/0048* (2013.01); *C04B 28/02* (2013.01); *G01B 5/30* (2013.01); *G01B 7/24* (2013.01); *G01N 33/383* (2013.01); *E04C 5/012* (2013.01)

(58) Field of Classification Search
CPC ... G01N 33/383; C04B 20/004; E04C 5/012; G01B 5/30
USPC .................... 73/760, 803; 428/362
See application file for complete search history.

(56) References Cited

U.S. PATENT DOCUMENTS

| | | | | |
|---|---|---|---|---|
| 4,050,949 A * | 9/1977 | Lundgren | ............. | C04B 14/005 106/643 |
| 5,989,713 A * | 11/1999 | Naaman | ................... | B29C 70/16 428/358 |
| 6,340,522 B1 * | 1/2002 | Burke | ..................... | E04C 5/012 428/359 |
| 2003/0044592 A1 * | 3/2003 | Perez | ...................... | C04B 16/06 428/294.7 |
| 2004/0038027 A1 * | 2/2004 | Lovett | ................. | C04B 16/0625 428/364 |
| 2005/0129931 A1 * | 6/2005 | Pilakoutas | .............. | E04C 5/012 428/332 |
| 2009/0075076 A1 * | 3/2009 | Li | ........................... | C04B 38/08 428/359 |
| 2015/0322664 A1 * | 11/2015 | Manning | ................... | E04B 5/32 52/742.15 |

* cited by examiner

*Primary Examiner* — Max Noori
(74) *Attorney, Agent, or Firm* — Brinks Gilson & Lione

(57) ABSTRACT

A method for designing and manufacturing micro reinforced concrete that produces a composite material that shares physical properties with both the reinforcing material and the concrete. Micro reinforced concrete is a two-part system that made of micro reinforcements, which are twisted steel fibers, and a concrete matrix. The micro reinforcements are added at a specified dose to an ordinary concrete matrix to create the micro reinforced concrete.

8 Claims, 7 Drawing Sheets

| Micro Reinforcement (MR) Specified | | | Minimum Average Count in 6x6 Beams | | |
|---|---|---|---|---|---|
| Boxes Added | Dosage (lb/yd$^3$) | Count (MR/in$^2$) | Class A & Cs | Class B | Class C |
| 1 | 5 | 1.2 | 10 | 13 | 10 |
| 2 | 10 | 2.4 | 25 | 28 | 23 |
| 3 | 15 | 3.6 | 44 | 46 | 38 |
| 4 | 20 | 4.8 | 64 | 63 | 53 |
| 5 | 25 | 6.0 | 86 | 79 | 68 |
| 6 | 30 | 7.3 | 110 | 95 | 82 |
| 7 | 35 | 8.5 | 133 | 111 | 95 |
| 8 | 40 | 9.7 | 157 | 127 | 109 |
| 9 | 45 | 10 | 181 | 143 | 123 |
| 10 | 50 | 12 | 204 | 159 | 136 |
| 11 | 55 | 13 | 228 | 175 | 150 |
| 12 | 60 | 14 | 251 | 191 | 164 |
| 13 | 65 | 15 | 274 | 207 | 177 |

Fig. 9

MICRO-REBAR CONCRETE REINFORCEMENT SYSTEM

CROSS REFERENCE TO RELATED APPLICATIONS

This application is the National Stage of International Application Serial No. PCT/US2013/076061 filed on Dec. 18, 2013, designating the United States and published in English, which claims the benefit of the filing date under 35 U.S.C. §119(e) of U.S. Provisional Application No. 61/738,483 filed Dec. 18, 2012, the entire contents of each of which are hereby incorporated herein by reference.

TECHNICAL FIELD

This present invention relates to reinforced concrete, and more specifically to the fiber reinforced concrete.

BACKGROUND

Concrete generally exhibits a low tensile strength and low fracture toughness. The ease with which cracks can nucleate and propagate in concrete under tension makes it imperative that, to the extent possible, concrete not be loaded in tension, and if unavoidable, some form of traditional reinforcement, such as rebar, be provided to take the tensile stresses. The latter is generally known as reinforced concrete.

An alternate method of reinforcement is by incorporating short, randomly distributed fibers in concrete such that the reinforcing fibers are distributed throughout the matrix and thus, a new composite material, known as micro- or fiber-reinforced concrete, is obtained. Fiber reinforced concrete has significantly improved energy absorption capability (often called toughness), impact resistance, and fatigue endurance, with greater resistance to cracking. It can also have better durability with an improved appearance.

Concrete has been reinforced with metal, steel and polymer fibers, in some cases strengthening the concrete and even making it blast resistant. Thread-like elements (fibers) of steel wire, having uniform corrugations along their entire length, have also been used for the reinforcement of concrete. Typically, steel fibers can be found in different forms: round (cut from wire), flat (sheared from steel sheets), and irregularly shaped from melt. Mechanical deformations such as crimping, adding hooks or paddles at their ends, or roughening their surface sometimes increases the bonding of the fibers to matrix.

Several problems have prevented fiber reinforced concrete from becoming widely adopted as a replacement for traditional steel reinforcement bar (rebar) and welded wire fabric. For example, straight fibers do not affect the concrete until large cracks develop, making them highly inefficient and not cost effective as compared to traditional reinforcement. Also, testing methods are not available for reliably characterizing tensile performance of fiber reinforced concrete. A physics based (not empirical) design approach, one that yields economically practical, safe and reliable designs while fully recognizing all limitations that gives engineers the confidence to specify micro rebar, has never been available. Finally, there is no method available to verify the distribution of the fibers in concrete to assure compliance with the specified design.

The combination of these shortfalls has limited fibers to use as shrinkage and temperature reinforcement in slabs on grade. While fibers have been implemented beyond slabs and have been used to replace tensile reinforcement in concrete, their acceptance has been limited by the problems described above.

SUMMARY

The present disclosure provides a micro reinforcement concrete system that uses twisted steel fibers (such as those disclosed in U.S. Pat. Nos. 6,060,163 and 5,989,713 and PCT Application No. PCT/US2012/055567, each of which is herein incorporated by reference) along with a way to characterize its tensile performance and develop designs that are reliable and more economical than typical steel fiber concrete.

In one aspect the present invention provides a design method for micro fiber reinforced concrete structures, the design method using an estimated number of twisted steel fibers in the micro reinforced concrete, the method comprising:

formulating tables that relate standard reinforcement bar cross section areas required to carry a tensile load to a required number of twisted steel fibers required to carry the same tensile load;

formulating tables that relate the required the number of twisted steel fibers to a dosage requirement to assure that a minimum number of the twisted steel fibers required to carry the load are present in the micro reinforced concrete;

computed load and resistance design (a statistical analysis of variance and reliability);

formulating a table that provides stable tensile stress provided by the twisted steel fibers as a function of the number of the twisted steel fibers;

monitoring strain to verify that the twisted steel fibers are behaving in the elastic and perfectly plastic region prior to crack formation, wherein a strain limit is based on the % increase versus baseline (plain concrete) in direct tension testing; and wherein all twisted steel fibers in the micro reinforced concrete define angles greater than 30 degrees to a plane perpendicular to an applied tensile load add the same tensile resistance to the micro reinforced concrete and wherein all twisted steel fibers defining angles less than 30 degrees to the plane perpendicular to the applied tensile load add no tensile resistance.

In another aspect, the present invention provides a direct tension test and analysis for micro reinforced concrete having twisted steel fibers in a concrete matrix, the test being a function of the number of twisted steel fibers in a broken cross section vs load at a design crack width (Sa), the test comprising:

forming a micro reinforced concrete test specimen having an hourglass shape and designed to be free of stress concentration, the forming of the test specimen being done in three pours of concrete containing the twisted steel fibers thereby preventing uneven distribution of twisted steel fibers in the test specimen;

estimating a stable force just prior to crack formation by multiplying by a factor of 2 the force at Sa, wherein the force is calculated assuming a twisted steel reinforcement with an embedded length of L/2 versus an elongated length of L/4 when a crack has formed.

In a further aspect, the present invention provides a micro reinforcement comprised of a twisted steel fiber having elastic, perfectly plastic behavior up to the point of dominant crack formation in a concrete matrix reinforced by the micro reinforcement, the twisted steel fiber further having stable tensile resistance after dominant crack formation up to a characteristic length determined by length, material used to manufacture and the number of twists provided in the twisted steel fiber, wherein the twisted steel fiber meets the following criteria:

a strain capacity increase requirement determined by tensile test results indicating a statically significant increase (minimum of 95% confidence, the maximum p-value in a two sample t-test, 0.05) in tensile strain capacity versus structural plain concrete, wherein a minimum of six control (plain concrete) specimens are considered in the analysis in addition to a minimum number of twisted steel fiber samples; and a post-crack tensile stability requirement determined by tensile test results indicating that the median of a load carried at Sa (design crack width) of the test specimen divided by a maximum load after 0.01 in displacement is equal to or greater than 0.85, wherein the twisted steel fiber crack width, Sa, is the crack width resulting from tensile stresses typically measured for structural design applications and represents the average upper limit of displacement in a direct tension test where the stress remains stable, wherein Sa is set forth as:

$$Sa = \delta + X/3 \qquad \text{(Eq.-1)}$$

where:
δ=material elongation as stated on raw material certification test reports, inch (mm)
X=elongation from twist, representing the materials approximate ability to "stretch" and need not be exactly determined, inch (mm)

$$X = 1 - \cos\left(a\tan\left(\frac{n2\pi d}{l}\right)\right) \qquad \text{(Eq.-2)}$$

and where:
n=number of full twists in the twisted steel fiber
d=equivalent diameter of the twisted steel fiber, inches (mm)
L=length of the twisted steel fiber, inches (mm)
X=percentage reduction in length from twisting of the twisted steel fiber and where:
the resulting values of Sa are used as a reference point for computing tensile resistance and compute maximum allowable crack width.

In yet another aspect, the micro reinforcement is combined in a concrete matrix forming a micro reinforced concrete used in a concrete structure in a tensile application, and wherein the tensile application experiences a maximum tensile strain that is less than a predetermined tensile strain limit for the micro reinforced concrete.

In still another aspect, the micro reinforcement is combined in a concrete matrix forming a micro reinforced concrete used for tensile resistance of principle tensile stresses.

In an additional aspect, the micro reinforcement is combined in a concrete matrix forming a micro reinforced concrete used in a concrete structure in combination with rebar or welded wire fabric to provide additional tensile resistance.

In another aspect, the present invention provides a design class system for micro reinforced concrete, the design class system comprising a series of design classes, the design classes being based on maximum allowable tensile strain and the presence or absence of at least one of soil support, lateral support or arch geometry.

In still another aspect, the present invention provides a method for measuring the distribution of the twisted steel fibers in a micro reinforced concrete structure, the method comprising the steps of:

one of preparing a beam or taking a core sample;
slicing the beam or core sample to expose a cross section of the beam or core sample; and
counting visible twisted steel fibers in the exposed cross section;
comparing the number of twisted steel fibers visible in a cross section to a table of limits based a given dosage, a factor of safety and a ratio of visible twisted steel fibers in the cross section.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 9 is a table illustrating the dosage and distribution limits for the various application classes.

DETAILED DESCRIPTION

As used throughout the referenced drawings, like references numerals indicate like elements. Also, it will be appreciated that individual elements of one embodiment may be removed or added to another embodiment, with or without other elements from the embodiment with which it is described.

Figure 1:
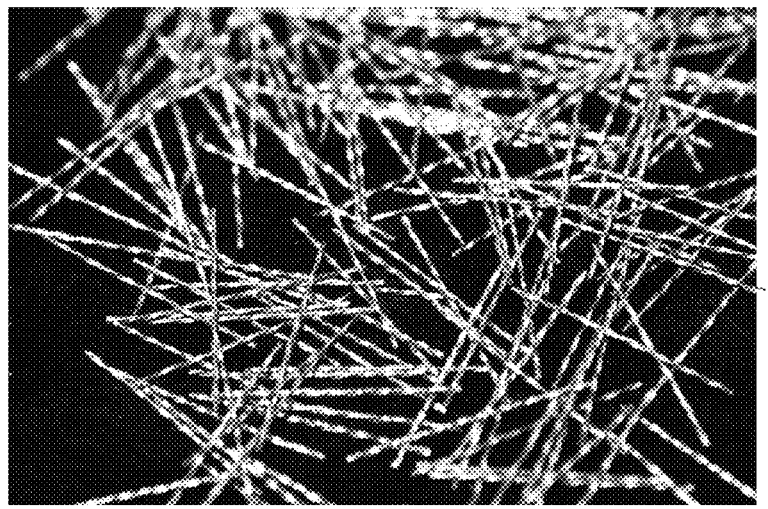
FIG. 1 is a photograph of micro reinforcements exhibiting twists along the length of the fibers.

According to the present invention, micro reinforcements (10) are steel fibers produced with a twisted profile (as generally seen FIG. 1) that allows each fiber to bond with the concrete matrix (12) over its full length. In addition, the micro reinforcement (10) must untwist as it pulls out of the concrete (12). This makes this resulting concrete product significantly different than one reinforced with traditional steel fibers (straight or ringed) because pullout in the present instance is governed by twisting resistance, rather than friction.

According to the present invention, the preferred micro reinforcements (10) have elastic, perfectly plastic behavior up to the point of dominant crack formation in the micro reinforced concrete (14) and have stable tensile resistance after dominant crack formation up to a characteristic length of the micro reinforcement (10), as determined by its length, material used for manufacture and the number of twists. The micro reinforcements (10) meet the following criteria:

1. Strain Capacity Increase Requirement: Tensile test results shall indicate a statically significant increase (minimum of 95% confidence, the maximum p-value in a two sample t-test, 0.05) in tensile strain capacity versus structural plain concrete. A minimum of six control (plain concrete) specimens shall be considered in the analysis in addition to a minimum number of micro reinforcement samples. Since resolution of data can be an issue in measurements of small deflections, data with slope coefficient of variation (COV) greater than 2 percent, as computed according to ASTM E111 Section 9.2 Equation 4, may be neglected.
2. Post-Crack Tensile Stability Requirement: Tensile tests shall indicate that the median of the load carried at Sa divided by the maximum load after 0.01 in displacement is equal to or greater than 0.85. Twisted Steel Micro Rebar Design Crack Width, Sa: This is the crack width resulting from tensile stresses typically measured for structural design applications. Sa represents the average upper limit of displacement in a direct tension test where the stress remains stable. Sa is set forth in Eq.-1:

$$Sa = \delta + X/3 \qquad \text{(Eq.-1)}$$

where:
δ=material elongation, as stated on raw material certification test reports, inch (mm)
X=elongation from twist, representing the materials approximate ability to "stretch" and need not be exactly determined, inch (mm)

$$X = 1 - \cos\left(a\tan\left(\frac{n2\pi d}{l}\right)\right) \qquad \text{(Eq.-2)}$$

where:
n=number of full revolutions of the part;
d=equivalent diameter of the wire, inches (mm);
L=length of the part, inches (mm);
X=percentage reduction in length from twisting the part; and where the resulting values of Sa are used as a reference point for computing tensile resistance and compute maximum allowable crack width. In general the larger the Sa selected, the smaller the tensile resistance and the larger the maximum allowable crack width.

Throughout this description, the described strains are based on deformation of the concrete, both before and after formation of a dominant crack. The limit of usable strain in the micro-reinforced concrete (14) is equivalent to a strain of 0.005 (500 micro-strain) in standard reinforcing bars (standard rebar). This equates to a crack opening in the micro-reinforced concrete of 0.001 in. (0.025 mm).

In addition, stress in the concrete (14) is based on engineering stress (tensile load divided by a plane area of concrete under consideration). For example, the engineering stress in a test coupon or test specimen (16) is computed by dividing the total applied load by the minimum cross sectional area of the neck (18) of the coupon. After a dominant crack occurs, the engineering stress is still based on the original minimum cross sectional area of the test specimen.

Figure 2:
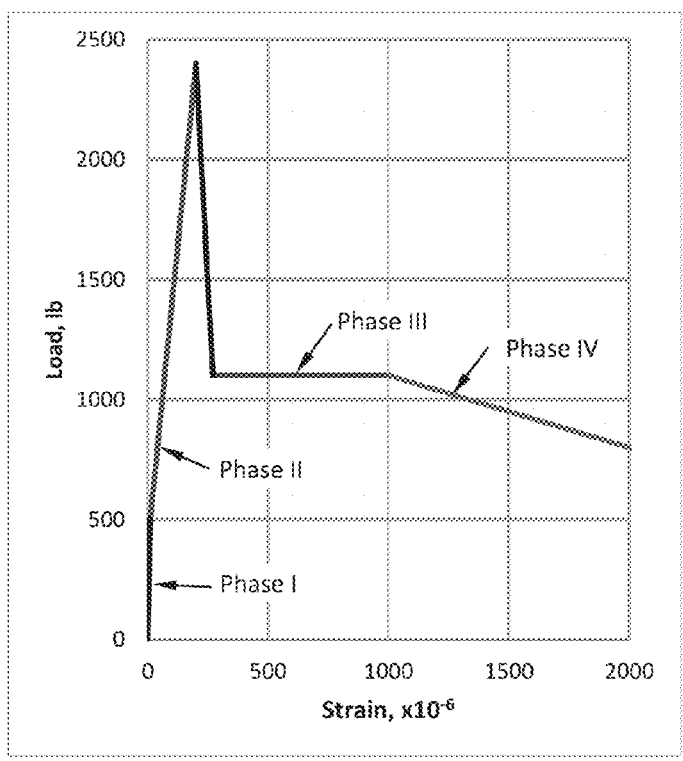
FIG. 2 is an idealized direct tension load deflection curve.
Figure 3:
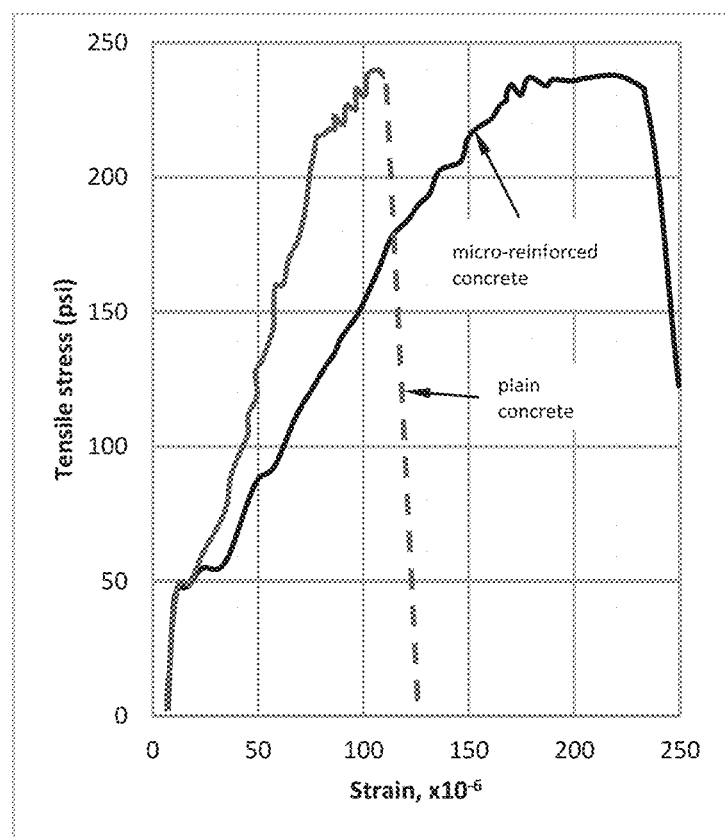
FIG. 3 illustrates phases I and II for both plain concrete and micro-reinforced concrete.

The performance of a micro-reinforced concrete composite (14) in tension is described using a multiphase approach. When loaded in tension, it has been found that micro-reinforced concrete (14) goes through four fundamentally different phases prior to the onset of complete fracture. FIG. 2 shows the four phases as they appear on an idealized load deflection curve of a direct tension test. The four phases may be summarized as follows:

Phase I—the micro-reinforced concrete (14) carries the tensile load until the first micro crack forms (0-10 microstrain); Phase II—the micro reinforcements (10) begins taking up load, herein referred to as proactive reinforcement, allowing additional micro cracking of the micro-reinforced concrete (14) as load is distributed among the fibers (10-200 microstrain); Phase III—micro crack localization causes the micro reinforcements (10) to carry the entire load and begin to elongate within the crack openings. In this phase, the engineering stress in the concrete matrix is a function of the micro reinforcement dosage (200-1000 microstrain); and Phase IV—the ends of the micro reinforcements (10) begin to move relative to the matrix (12) (>1000 microstrain). Comparing plain concrete and micro-reinforced concrete (14) (as seen in FIG. 3), we find that both materials are quite stiff in Phase I until micro cracking initiates at about 10 microstrain. Tests show that this onset of micro cracking corresponds to a tensile stress of about 50 psi (0.34 MPa). In plain concrete, Phase II ends with micro crack localization and failure at about 100 microstrain. But in micro-reinforced concrete (14), it has been found that the load is redistributed across the micro cracks. As the stress increases above 50 psi (0.34 MPa), the redistribution of the load to the micro reinforcements (10) results in a slight softening of the composite, which delays micro crack localization, allowing the composite to resist well over 200 microstrain before the formation of a dominant crack is observed. Analysis of direct tension tests has shown that this increase in strain capacity is statistically significant, with a confidence level of over 99%.

In Phase III (as shown in FIG. 2), it's important to note that the micro reinforcements (10) begin to stretch, but do not pull out of the concrete matrix (12). Pullout begins in Phase IV. As strain increases during the final phase, the micro-reinforced concrete (14) softens incrementally as individual micro reinforcement pieces untwist and pull out of the matrix.

Performance Characterization

Figure 4A:
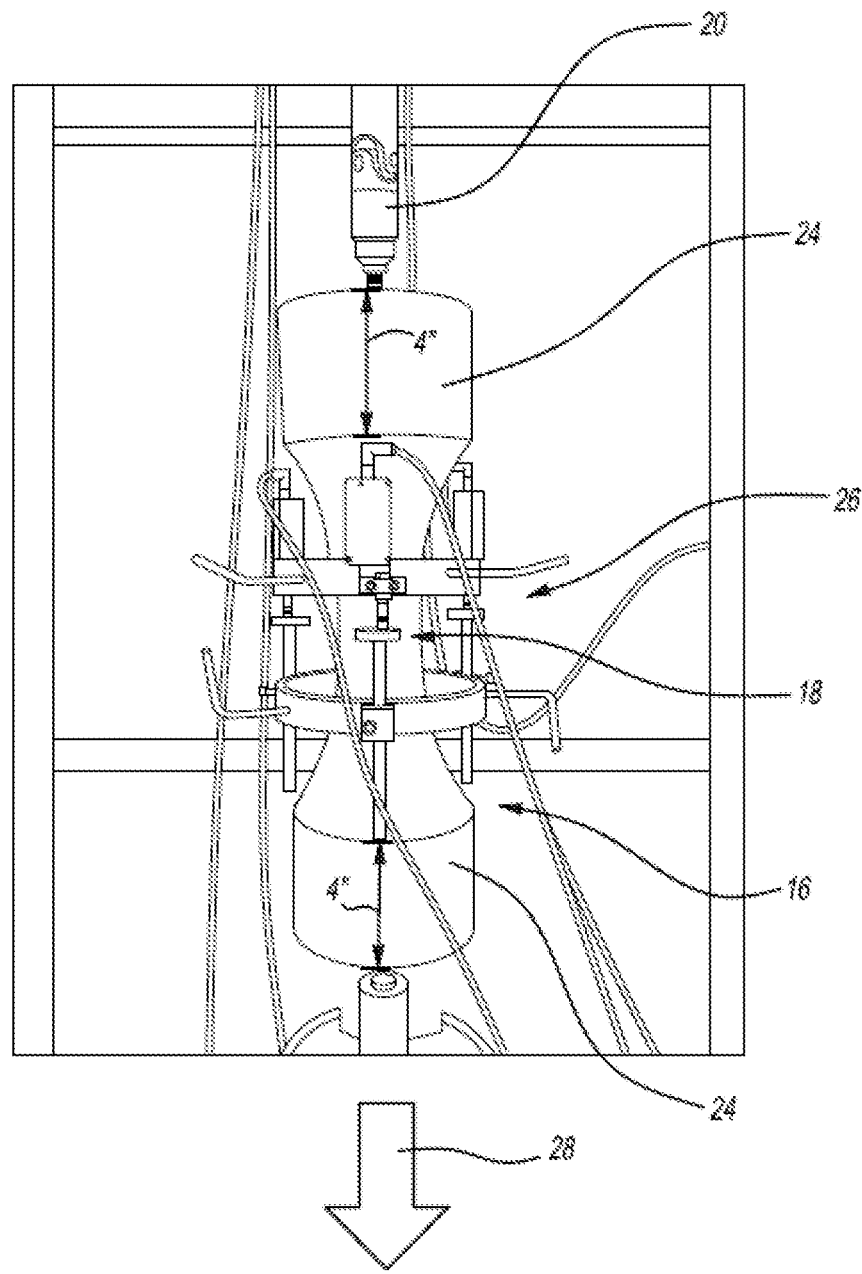
FIG. 4A is a photograph of testing assembly for a direct tension test setup.
Figure 4B:
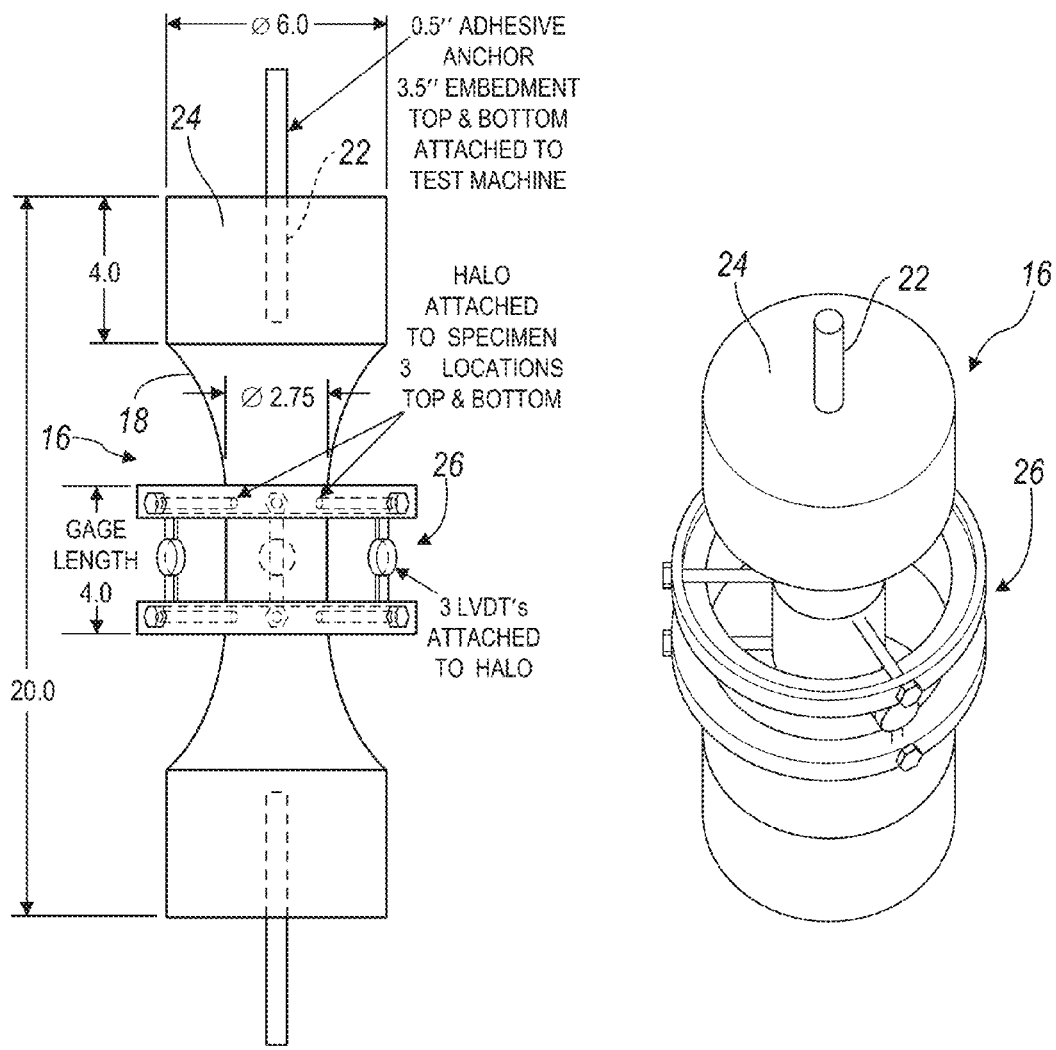
FIG. 4B illustrates the specimen to be used for the direct tension test.

Tensile resistance is the primary engineering parameter needed for design with micro-reinforced concrete (14). While beam tests have been the traditional way to evaluate fiber-reinforced concrete, stresses must be calculated using the section properties for the un-cracked section. Because the fiber stresses vary over the depth of the specimen (both before and after cracking), the flexural test doesn't adequately measure the performance of micro-reinforced concrete. According to the present invention, direct tension tests are applied to evaluate micro-reinforced concrete (14), using a load frame (20) and a cylindrical tensile test specimen (16) as shown in FIGS. 4A and 4B. The reduced gauge section or neck (18) of the test specimen (16) has large fillet radii to minimize stress concentrations and encourage the development of a dominant crack in the center of the reduced gauge section (18). Load is applied through adhesive anchors (22) embedded in the grip zone or ends (24) of the test specimen (16). Strain is monitored using a strain gauge (26) (comprised of three or four linear variable differential transducers (LVDT) between gage heads and having a 4 in. (100 mm) gauge length). The specimen is pulled under displacement control until it reaches an engineering strain of 1% (1000 microstrain). The test setup and instrumentation are capable of accurately measuring strain both before and after the formation of a dominant crack. The data collected in the direct tension test is a load deflection plot, similar to what is shown in FIG. 2. After fracture, the number of micro reinforcements crossing the failure plane is counted, and the load determined. As discussed in the following section, the results of this test are not related to a particular dosage rate—only the load per micro reinforcement element.

During production of test specimens (16), micro reinforcements (10) within the reduced gauge section (18) tend to align parallel to the axis of the test specimen (16) and the direction of the applied load (28). Inspection of broken specimens and geometric analyses, using Monte-Carlo simulations, indicate that 88% of the micro reinforcements (10) crossing the dominant crack are at inclination angles greater than 30 degrees to the crack surface (to a plane perpendicular to the applied load (28)). It has also been discovered that micro reinforcements (10) having inclination angles of at least 30 degrees will fail by pulling out of the concrete, rather than fracturing. Thus, the total force applied to the test specimen will be proportional to the number of micro reinforcements crossing the dominant crack and having inclination angles greater than 30 degrees.

Since the mold for the test specimens (16) affects the quantity of micro reinforcements (10) crossing the failure surface, a separate test is needed to more generically link a dosage rate of micro reinforcements to the number of micro reinforcements per square inch (square meter) of fracture area. This has been accomplished by counting the micro reinforcements (10) crossing the failure plane for a beam specimen produced and tested according to ASTM C78, "Standard Test Method for Flexural Strength of Concrete (Using Simple Beam with Third-Point Loading)."

Figure 5:
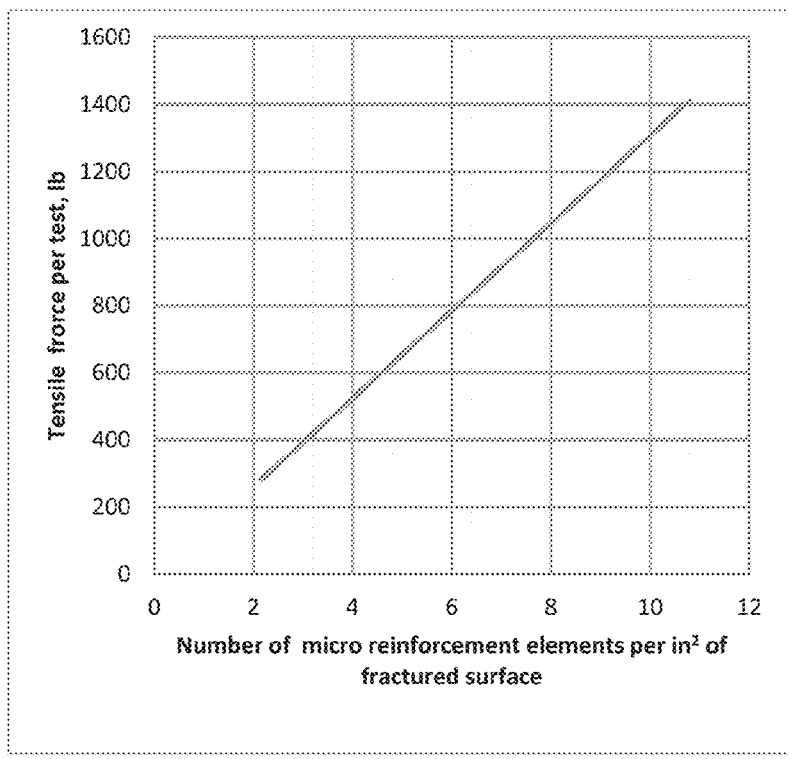
FIG. 5 is an example of the best fit relationship for tensile forces.

Using mixtures with a range of micro reinforcement dosages, the inventors have developed relationships for total tension load (strains up to 1000 microstrain) as a function of the compressive strength of the micro reinforced concrete (14) and the number of micro reinforcements (10) crossing the dominant crack surface at angles of 30 degrees or more. FIG. 5 shows the tensile force as a function of number of micro reinforcements (10) crossing the fracture surface. This example is for a micro reinforced concrete mixture with a 4000 psi (27.6 MPa) compressive strength.

Proactive and Reactive Reinforcement

As previously mentioned, "proactive" reinforcement is when a micro reinforcement (10) begins taking on a load prior the formation of a dominant crack. Common examples of proactive reinforcement include the glass or carbon fibers in fiber-reinforced polymers. In these composite materials, the fibers dominate the physical properties. In contrast, the reinforcing bars (rebar) in traditional reinforced concrete provide only reactive reinforcement—they have no significant effect on the properties of the composite of concrete and steel prior to the development of a crack.

Figure 6:
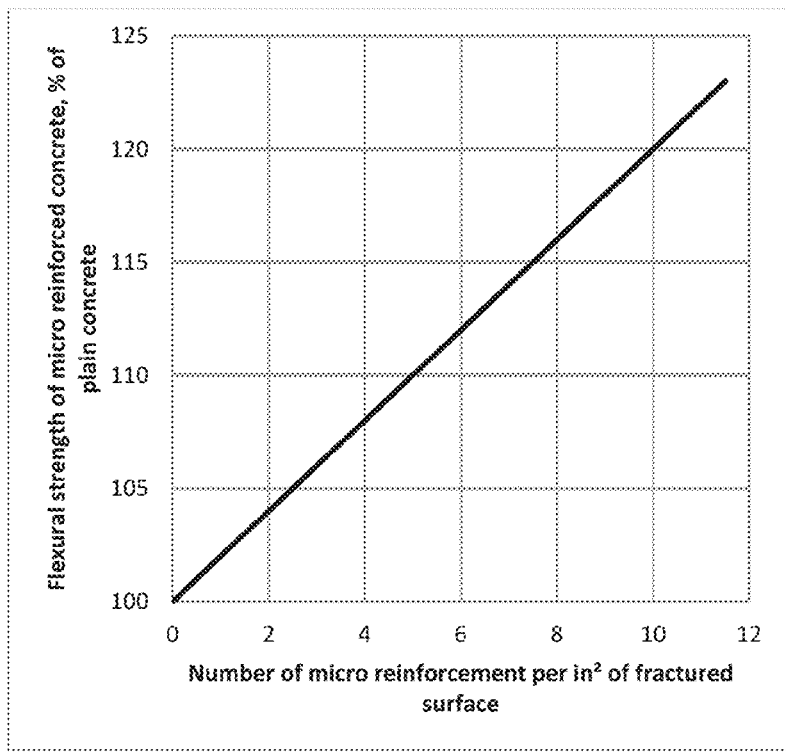
FIG. 6 illustrates the modulus of rupture as a function of the micro reinforcement count in the concrete.

The unique geometry of the micro reinforcements (10) provides superior bond, allowing it to act as proactive reinforcement (Phase I and II in FIGS. 2 and 3). With increasing dosages, the modulus of rupture increases (FIG. 6, showing the modulus of rupture as a function of crossing the fracture surface). While this increase is not considered in design, the stable post-cracking behavior of micro-reinforced concrete (Phase III in FIG. 2) mimics the stable tensile response of traditional reinforcing bars in concrete, allowing use of the standard design equations typically utilized for reinforced concrete and greatly simplifying the design approach.

Design

While micro reinforcements (10) offer unique advantages in concrete due to their ability to provide proactive response, according to the present invention, it is designed using the same cracked section assumptions as for standard reactive reinforcement.

Micro reinforcement design is accomplished with four simple steps:

Computation of the area of traditional steel reinforcing required for temperature and shrinkage reinforcement or flexural reinforcement;

Selection of the micro reinforcement design class;

Determination of the required number of micro reinforcements; and

Calculation of micro reinforcement dosage per unit volume of concrete.

Figure 8:
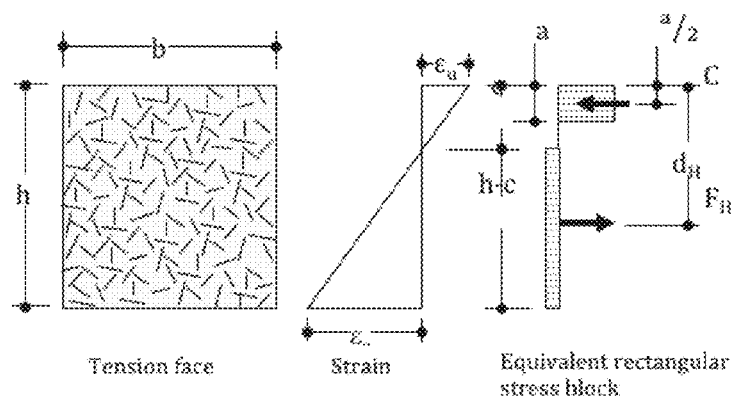
FIG. 8. is a flexural stress block diagram.

The micro reinforcement contribution to the tensile behavior of the concrete (14) (characterized by the previously described testing) is applied as a rectangular stress block in the tensile zone of the concrete section (see FIG. 8, force equilibrium and strain compatibility diagram). The first step requires that the engineer uses standard design equations to compute the nominal area of steel traditionally required at the centroid of the tensile region.

Figure 7:
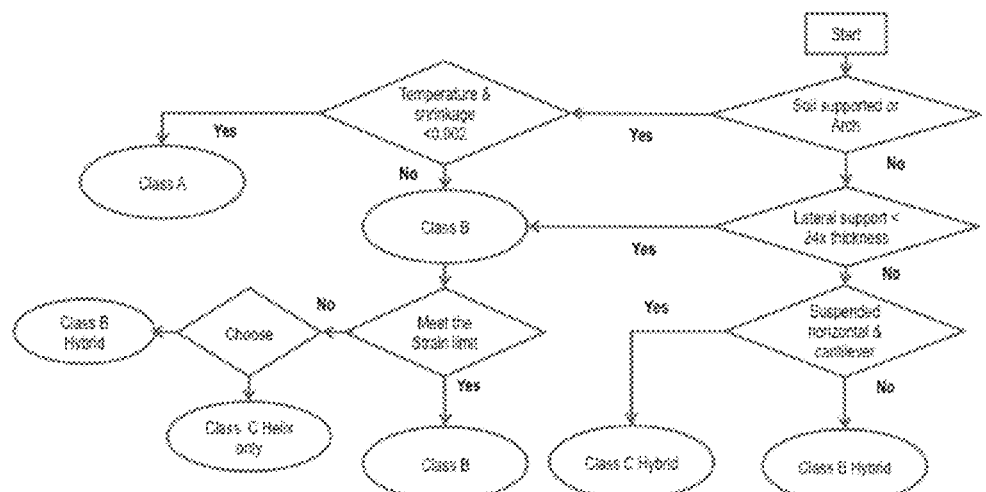
FIG. 7 is a flow chart illustrating the process for determining the classification of applications for micro reinforced concrete.

The classes for micro reinforcement design are based on the support and geometric conditions of the application. Soil-supported structures, requiring only temperature and shrinkage reinforcement, are Class A applications. Structural concrete that is soil supported, carries load such as an arch, or is in a vertical component with closely spaced lateral supports, is considered a Class B application. All other structural applications, including suspended concrete floors, are Class C applications. Class C applications require reinforcing bars to provide load redistribution capacity. The flowchart shown in FIG. 7 can be used as a guide for determining the design class for particular applications.

Once the design class is known, the number of micro reinforcements required to resist the tensile load (in the much same way as one determines the quantity of reinforcing bars required in a section) is calculated. To simplify the design process, the required micro reinforcement quantities have been tabulated based on the characterization data obtained from direct tension testing (see examples in FIG. 8).

Finally, the required micro reinforcement dosage (weight of fibers per unit volume of concrete) is calculated based on the cross sectional area loaded in tension (see FIG. 8). The micro reinforcement dosages are based on limit state design methods, with load factors consistent with standard building practice. Dosages selected for Class A and C have been chosen to provide concrete strengths that match the average strength values as recommended in ACI 360 R4 and required by ACI 318-08, respectively.

Verification of micro reinforcement dosage in fresh concrete is accomplished, first, by assuring batch plant quality control (dosage included on batch tickets) and, second, by a washout test similar to the procedure outlined in the Canadian standard CSA A23.2-16C.

Micro reinforcement distribution verification testing, when required, may be done by saw-cutting or breaking three standard beam specimens, as described in ASTM C78 "Standard Test Method for Flexural Strength of Concrete (Using Simple Beam with Third-Point Loading)". In such verification testing, three specimens with dimensions of 6×6 inch (100 mm×100 mm) are made with concrete sampled from the middle portion of the batch. ASTM C172 "Standard Practice for Sampling Freshly Mixed Concrete" specifies that samples should not be taken before 10% or after 90% of the batch has been discharged and CSA A23.2-1C "Sampling Plastic Concrete" specifies that the three samples should be collected when 25%, 50% and 75% of the concrete batch is discharged.

If the verification specimen is saw-cut (preferred), the number of micro reinforcements exposed on one of the cut surfaces of each sample are counted. If the verification specimen is broken, the micro reinforcements protruding from both matching broken surfaces shall be counted, added together.

The average values of the three verification specimens constitute one verification sample and the micro reinforcement count should exceed the table value (see FIG. 9) for the design class used. The limits are computed by multiplying the design dosage by the resistance factor applied to the design. This factor changes based on dosage and design class.

Although 6×6 inch (100 mm×100 mm) beams are the preferable verification specimen size, other specimen sizes may be used. If an alternate verification specimen size is used, such as a smaller beams or cores, there should be at least 3 total specimens. A composite specimen may be made of several smaller specimens such that each composite specimens is at least 36 in$^2$ (22500 mm$^2$), the size of the preferable 6×6 inch (150 mm×150 mm) beam. The minimum size for any single verification specimen is 10 in$^2$ (6450 mm$^2$). So for example, one specimen could be made up of three (3) 4×4 inch beams, 16 in$^2$ each×3=48 in$^2$>36 in$^2$ (100 mm×100 mm, 10000 mm$^2$×3=30000 mm$^2$>22500 mm$^2$). To obtain the result for one specimen multiply the average count of all composite specimens by [36 in$^2$ (22500 mm$^2$)]/[Total Composite Specimen Cross Section Area].

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

What is claimed is:

1. A design method for micro fiber reinforced concrete structures, the design method using an estimated number of twisted steel fibers in the micro reinforced concrete, the method comprising:
   formulating tables that relate standard reinforcement bar cross section areas required to carry a tensile load to a required number of twisted steel fibers required to carry the same tensile load;
   formulating tables that relate the required the number of twisted steel fibers to a dosage requirement to assure that a minimum number of the twisted steel fibers required to carry the load are present in the micro reinforced concrete;
   computed load and resistance design (a statistical analysis of variance and reliability);
   formulating a table that provides stable tensile stress provided by the twisted steel fibers as a function of the number of the twisted steel fibers;
   monitoring strain to verify that the twisted steel fibers are behaving in the elastic and perfectly plastic region prior to crack formation, wherein a strain limit is based on the % increase versus baseline (plain concrete) in direct tension testing; and
   wherein all twisted steel fibers in the micro reinforced concrete define angles greater than 30 degrees to a plane perpendicular to an applied tensile load add the same tensile resistance to the micro reinforced concrete and wherein all twisted steel fibers defining angles less than 30 degrees to the plane perpendicular to the applied tensile load add no tensile resistance.

2. A direct tension test and analysis for micro reinforced concrete having twisted steel fibers in a concrete matrix, the test being a function of the number of twisted steel fibers in a broken cross section vs load at a design crack width (Sa), the test comprising:
   forming a micro reinforced concrete test specimen having an hourglass shape and designed to be free of stress concentration, the forming of the test specimen being done in three pours of concrete containing the twisted steel fibers thereby preventing uneven distribution of twisted steel fibers in the test specimen;
   estimating a stable force just prior to crack formation by multiplying by a factor of 2 the force at Sa, wherein the force is calculated assuming a twisted steel reinforcement with an embedded length of L/2 versus an elongated length of L/4 when a crack has formed.

3. A micro reinforcement comprised of a twisted steel fiber having elastic, perfectly plastic behavior up to the point of dominant crack formation in a concrete matrix reinforced by the micro reinforcement, the twisted steel fiber further having stable tensile resistance after dominant crack formation up to a characteristic length determined by length, material used to manufacture and the number of twists provided in the twisted steel fiber, wherein the twisted steel fiber meets the following criteria:
   a. a strain capacity increase requirement determined by tensile test results indicating a statically significant increase (minimum of 95% confidence, the maximum p-value in a two sample t-test, 0.05) in tensile strain capacity versus structural plain concrete, wherein a minimum of six control (plain concrete) specimens are considered in the analysis in addition to a minimum number of twisted steel fiber samples; and
   b. a post-crack tensile stability requirement determined by tensile test results indicating that the median of a load carried at Sa (design crack width) of the test specimen divided by a maximum load after 0.01 in displacement is equal to or greater than 0.85, wherein the twisted steel fiber crack width, Sa, is the crack width resulting from tensile stresses typically measured for structural design applications and represents the average upper limit of displacement in a direct tension test where the stress remains stable, wherein Sa is set forth as:

$$Sa = \delta + X/3 \quad \text{(Eq. 1)}$$

where:
   $\delta$=material elongation as stated on raw material certification test reports, inch (mm)
   X=elongation from twist, representing the materials approximate ability to "stretch" and need not be exactly determined, inch (mm)

$$X = 1 - \cos\left(\operatorname{atan}\left(\frac{n2\pi d}{l}\right)\right) \quad \text{(Eq. 2)}$$

and where:
   n=number of full twists in the twisted steel fiber
   d=equivalent diameter of the twisted steel fiber, inches (mm)
   L=length of the twisted steel fiber, inches (mm)
   X=percentage reduction in length from twisting of the twisted steel fiber and where:
the resulting values of Sa are used as a reference point for computing tensile resistance and compute maximum allowable crack width.

4. The micro reinforcement of claim 3, wherein the micro reinforcement is combined in a concrete matrix forming a micro reinforced concrete used in a concrete structure in a tensile application, and wherein the tensile application experiences a maximum tensile strain that is less than a predetermined tensile strain limit for the micro reinforced concrete.

5. The micro reinforcement of claim 3, wherein the micro reinforcement is combined in a concrete matrix forming a micro reinforced concrete used for tensile resistance of principle tensile stresses.

6. The micro reinforcement of claim 3, wherein the micro reinforcement is combined in a concrete matrix forming a micro reinforced concrete used in a concrete structure in combination with rebar or welded wire fabric to provide additional tensile resistance.

7. A design class system for micro reinforced concrete, the design class system comprising a series of design classes, the design classes being based on maximum allowable tensile strain and the presence or absence of at least one of soil support, lateral support or arch geometry.

8. A method for measuring the distribution of the twisted steel fibers in a micro reinforced concrete structure, the method comprising the steps of:
one of preparing a beam or taking a core sample;
slicing the beam or core sample to expose a cross section of the beam or core sample; and
counting visible twisted steel fibers in the exposed cross section;
comparing the number of twisted steel fibers visible in a cross section to a table of limits based a given dosage, a factor of safety and a ratio of visible twisted steel fibers in the cross section.

* * * * *